United States Patent [19]

Siegel

[11] Patent Number: 4,872,752
[45] Date of Patent: Oct. 10, 1989

[54] DIAGNOSIS OF FREE FATTY ACID TOXICITY BY MONITORING RED BLOOD CELLS MORPHOLOGIC CHANGES

[76] Inventor: Israel Siegel, 5313 Collins Ave. Apr. 412, Miami Beach, Fla. 33140

[21] Appl. No.: 100,287

[22] Filed: Sep. 23, 1987

Related U.S. Application Data

[63] Continuation-in-part of Ser. No. 713,861, Mar. 20, 1985, abandoned.

[51] Int. Cl.[4] ............................................. G01N 33/48
[52] U.S. Cl. ...................................... 356/39; 436/811
[58] Field of Search ................... 436/63, 66, 174, 179, 436/815, 811

[56] References Cited

PUBLICATIONS

Siegel et al., "Defense Against Infection–A Selective Role for Unsaturated Fatty Acid" (Symposium Abstracts) Am. J. Reprod. Immunol. 3(4):197 (1983).

Greisman, "Hyperlipemia and Hemolysis I. Interaction of Sodium Oleate with Human Erythrocytes" Proc. Soc. Exp. Biol. Med. 101:117–122 (1954) (see first paragraph, p. 177).

Ross et al., "Acquired Stomatocytosis in Infants Receiving Parenteral Fat Emulsion" Pediatr. Res. 12 (4II) 473 (1978).

Siegel et al., "Parenteral Fat Emulsions and Immune Adherence" JAMA251(12)1574–1579 (03/23/84).

Primary Examiner—H. M. S. Sneed
Assistant Examiner—James Shi

[57] ABSTRACT

The present invention consists of a method for diagnosing free fatty acid toxicity, particularly resulting from parenteral fat emulsion. Specifically, red cell morphology is microscopically monitored to detect specific abnormal alterations resulting from various degrees of free fatty acid toxicity.

6 Claims, 2 Drawing Sheets

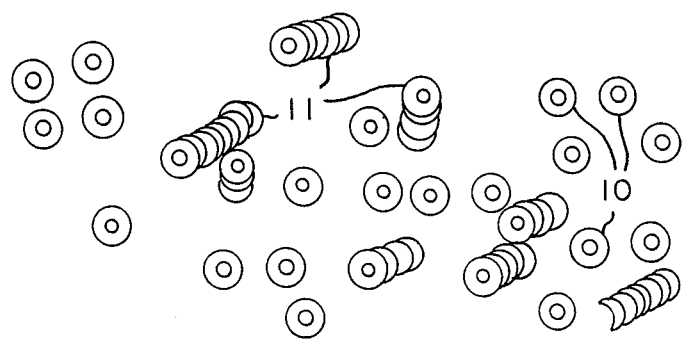
FIG. 1
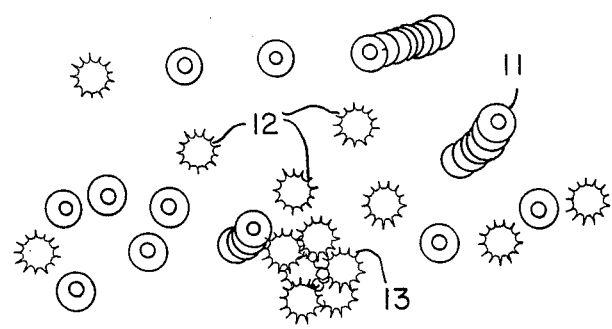
FIG. 2
FIG. 3
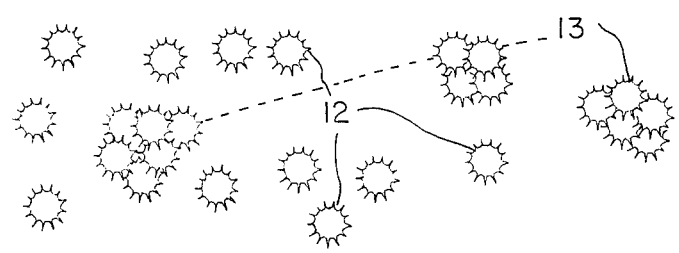

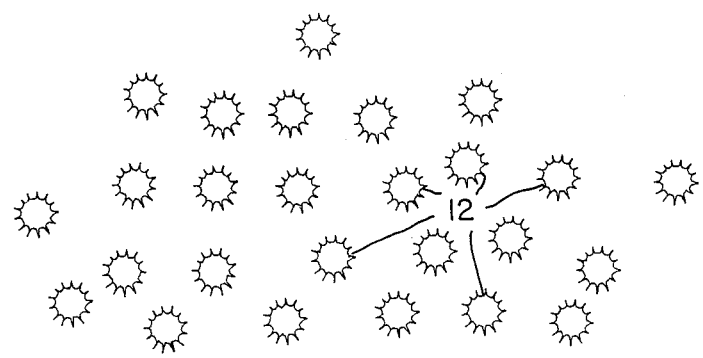
FIG. 4
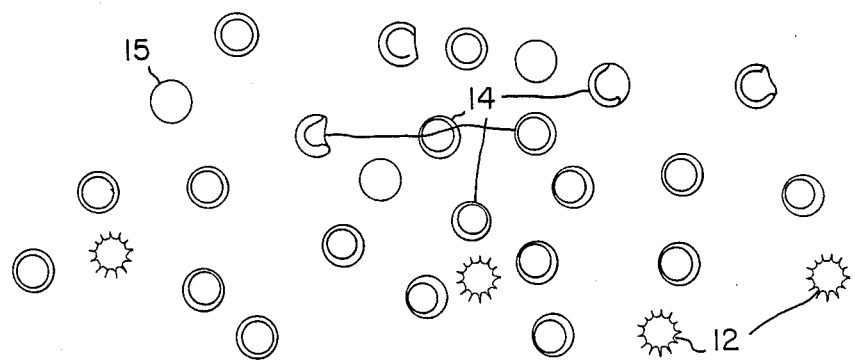
FIG. 5
FIG. 6
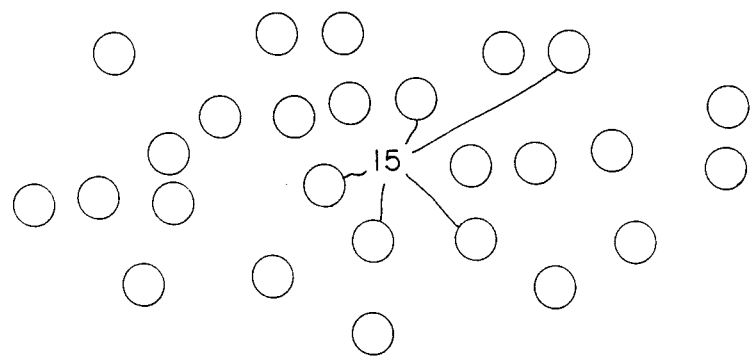

DIAGNOSIS OF FREE FATTY ACID TOXICITY BY MONITORING RED BLOOD CELLS MORPHOLOGIC CHANGES

This is a continuation in part of my earlier filed patent application, Ser. No. 713,861, filed Mar. 20, 1985 now abandoned.

FIELD OF INVENTION

The invention relates to methods for monitoring side effects of parenteral fat emulsions and in particular to monitoring of free fatty acid toxicity.

BACKGROUND ART

Fat emulsions have been widely used components of total parenteral nutrition because of their high caloric value, their isotonic properties, and their contents of essential fatty acids. A wide spectrum of patients are likely to receive the fat emulsions. These consist of patients with any clinical condition which prevents a satisfaction of caloric needs through the enteric route. The ages of patients who may be treated with fat emulsions range from premature infants to geriatric patients close to the end of their natural life span.

Triglycerides of fat emulsion are hydrolyzed by lipases in the plasma into metabolites which are among the biologically most toxic compounds on earth. These metabolites are the free or unesterified fatty acid molecules (FFA). The characteristics of the FFA have been reviewed in a recent article of the author of this invention and co-worker (*Fertility and Sterility*, Volume 45, pp. 273–279, Feb. 1986). FFA molecules are known to be toxic to red cells, white cells, heart cells, brain cells, and a variety of other cell types.

Despite their toxic properties the FFA molecules are essential for several physiologic systems. They are the major metabolite through which energy is obtained from dietary and physiologic fat molecules, and they are incorporated into phospholipids and other molecules to form components of cell membranes. In addition, they participate in defense mechanisms and in regulation of immune responses.

The coexistence of life with toxic FFA molecules is possible because of homeostatic mechanisms which neutralize fatty acid toxicity and regulate the concentration of the free fatty acid molecules. Under normal conditions the plasma contains an average FFA concentration of 0.4–0.8 mEq/l with a range of 0.315–1.218 mEq/l. The major plasma component which neutralizes fatty acid toxicities is albumin. The ability of albumin to efficiently neutralize FFA toxicity in the plasma seems to be limited to about two free fatty acids per albumin molecule. The normal range of FFA/albumin ratios is 0.5–2. When the ratio exceeds 2 the toxic effects of fatty acids become evident in a variety of essential physiologic systems.

For example, an FFA/albumin ratio of 2–3 inhibits chemotaxis of neutrophils by about 50%, makes platelets more susceptible to aggregation, and cause morphologic and immune changes in the red cells. A ratio of 3 was demonstrated to depress the contractility of rat heart preparations, a ratio of 4 depresses phagocytosis and bactericidal abilities of neutrophils, and displaces bound bilirubin from albumin molecules. This increases the risk of kernicterus in infants. A ratio of 5 changes enzymatic patterns in perfused heart muscle. A ratio of 6–7 causes heart beat abnormalities in patients with myocardial infarctions.

Studies of fluctuations of FFA during administration of parenteral fat emulsion have indicated that free fatty acids may reach levels known to be toxic to cells. For example, Andrew, et al. (*Journal of Pediatrics*, volume 88, page 273–277, 1976), infused infants within the first 48 hours of birth with 1 g/kg of Intralipid over a four hour period. This resulted in a mean FFA/albumin ratio of $10.75 \pm 2.19$ in 7 small for gestational age infants. In 10 appropriate for gestational age infants of less than 33 weeks gestational age the FFA/albumin ratio was $4.99 \pm 0.37$. In 10 appropriate for gestational age infants over 33 weeks the FFA/albumin ratio was $3.88 \pm 0.37$. Such high ratios are most likely to result in clinically significant side effects.

Factors which determine the release and removal of free fatty acid are numerous and complex. In the severely ill patient suffering from metabolic distortions, the effect of parenteral fat emulsion upon FFA levels may be especially hard or impossible to predict. A monitoring procedure which can be used to adjust the rate of fat emulsion infusion while the fat emulsion is being infused would constitute the most effective means for the prevention of excess accumulation of free fatty acids.

Standard biochemical methods currently available require specialized biochemical laboratories. The results are usually available to the clinician several days after the blood has been withdrawn from the patient. By that time the damage caused by the toxic concentrations of the free fatty acids had already taken place. This may result in additional suffering or even the death of the patient.

In addition, a minimum of several ml of blood are required for the biochemical analysis. This could rapidly deplete the small blood reserves of a premature or newborn infant who are receiving fat emulsion therapy.

One objective of the present invention is to devise an improved monitoring method which can utilize only one drop of blood to detect FFA toxicity. An additional objective of the present invention is to devise an FFA toxicity monitoring method which would yield results almost immediately after the blood has been withdrawn. A third objective of this invention is to devise a method which could detect FFA toxicity at very early stages of toxicity.

Essentially, the method described in this disclosure is based upon the observations that toxic free fatty acid/albumin ratios are reflected in the changes in red cell morphology. The red cells can therefore be used as sensitive indicators of FFA toxicity.

SUMMARY

Fat emulsions are commonly used as a main source of energy in patients receiving intravenous nutrition. The fat emulsion may increase the levels of free fatty acid in the blood of the patient to toxic levels. A monitoring technique to detect the presence of free fatty acid toxicity while the fat emulsion is being infused is the most efficient means of preventing a toxic accumulation of free fatty acid. Procedures currently available for the detection of free fatty acid concentrations require a relatively long time and relatively large volumes of blood, and are therefore not suitable for such monitoring procedures. The present invention describes a method which is designed to detect free fatty acid toxicity within minutes after only 1 drop of blood is obtained from the patient.

The monitoring procedure is based upon the fact that highly predictable morphologic changes occur in red cells in response to the toxic effects of free fatty acid. An infusion of fat emulsion is started in a patient at an infusion rate estimated to be optimal by the patient's physician. A drop of blood is obtained from the patient while the infusion takes place at various predetermined periods after the initiation of the fat emulsion therapy. The drop is transferred to a slide and covered with a coverslip to prevent drying of the blood. The slide is then observed to determine whether morphologic changes occurred in the red cells. The morphology of the red cells in the patients blood is then compared to the morphology of red cells in standards consisting of red cell serum mixtures with known free fatty acid concentrations. At least 5 stages of free fatty acid toxicity can be identified by the present method. The rate of fat emulsion infusion is then adjusted by the physician in charge according to the results of the monitoring procedures and the overall clinical state of the patient.

BRIEF DESCRIPTION OF THE DRAWINGS

FIGS. 1-6 illustrate the normal morphology of the red cells and the morphology of the red cells at 5 stages of free fatty acid toxicity. The figures represent typical morphology of red cells both in standard containing known FFA concentrations, and in patients receiving parenteral fat emulsion therapy.

FIG. 1 illustrates the morphology of the red cells in the absence of detectable FFA toxicity.

FIG. 2 illustrates the morphology of the red cells during a relatively early stage (Stage I) of FFA toxicity.

FIG. 3 illustrates the morphology of the red cells in the presence of more advanced (Stage II) FFA toxicity.

FIG. 4 illustrates the morphology of the red cells in the presence of an intermediate stage of FFA toxicity (Stage III).

FIG. 5 illustrates the morphology of the red cells in the presence of relatively advanced stages of FFA toxicity (Stage IV)

FIG. 6 illustrates the morphology of the red cells in the presence of very advanced stages of FFA toxicity (Stage V).

BEST MODE FOR CARRYING OUT THE INVENTION

The following is an example which illustrate the best mode of carrying out the invention. It is understood that the quantitative aspects and timings of the procedures may vary according to the individual need of the patient. This can only be determined by the physician who is familiar with the overall clinical status of the patient. Such variations, however, remain within the scope of the present invention as will be defined in the claims.

1. An intravenous infusion of 10% or 20% parenteral fat emulsion into a patient is begun at a standard rate of a total of 500 ml in 8 hours.

2. At 1 hour intervals after the initiation of the infusion the skin surface of the patient is pricked with a lancet to obtain one drop of blood.

3. A standard capillary tube coated with anticoagulant such as heparin is then used to aspirate the drop of blood.

4. The blood may then be transferred to a tube containing small quantities (e.g. 0.5 ml) of saline to decrease the concentration of red blood cells. This will facilitate the observation of individual red cells under the microscope.

5. A drop of the above mixture is transferred to a microscopic slide and covered with a coverslip to prevent the blood from drying during the observation period.

6. The slide is immediately observed under a phase microscope.

7. The shape of the red cells in the blood is then compared to the shape of red cells in standard mixtures containing known concentrations of FFA.

The morphology of the red cells in the standard mixtures are illustrated in FIGS. 1-6.

FIG. 1 illustrates the normal morphology of the red cells. Practically all of the red cells are in the form of discocytes (No. 10) and the red cells aggregate spontaneously to form rouleux (No. 11).

Under normal conditions with no FFA additions the red cells assume a biconcave shape and have therefore been called discocytes. The discocytes may spontaneously aggregate to form rouleux. This spontaneous aggregations is a normal phenomenon which occurs in stationary or slow moving red cells in plasma.

FIG. 2 illustrates the morphology of the red cells during a relatively early stage (Stage I) of FFA toxicity. Both discocyte (No. 10) and echinocytes (No. 12) are evident. The red cells have not lost the capacity to spontaneously aggregate. Both discocyte rouleux (No. 11) and echinocyte aggregates (no. 13) are evident in the mixtures.

This represents the first detectable morphologic effect upon the red cells which occurs upon the addition of 0.5-2 mEq/l of linoleic acid to the serum-red cell mixtures. The addition causes a proportion of the red cell population to develop surface spurs and to lose their biconcave shape. This is accompanied by varying degrees of cell shrinkage. The transformed red cells resemble red cell shapes which have been called echinocytes or spur cells. The red cells retain their ability to form spontaneous aggregates. Thus, the transformation of only a proportion of the red cell population to echinocytes can be identified through the presence of both echinocytes and discocytes in the red cell population. We have used this morphologic marker to identify early or Stage 1 FFA toxicity.

FIG. 3 illustrates the morphology of red cells in the presence of more advanced (Stage II) FFA toxicity. As can be seen, practically all of the red cells have transformed into echinocytes (No. 12). Spontaneous aggregates of echinocytes are evident (No. 13).

This occurs upon the addition of about 2 mEq of FFA which represents an increase of FFA/albumin ratio of about 3. The transformation of 100% of the red cells into echinocytes which retain their ability to spontaneously aggregate is thus a marker for the identification of Stage II FFA toxicity.

FIG. 4 illustrates the morphology of the red cells in the presence of an intermediate stage of FFA toxicity (Stage III). All the red cells have transformed to echinocytes (No. 12). The echinocytes have lost their ability to spontaneously aggregate.

Thus, the presence or absence of spontaneous red cell aggregates can help distinguish between Stage II and Stage III FFA toxicities. The morphologic features of Stage III cytotoxicity were evident in serum-red cell mixtures which contained 4 mEq of linoleic acid. This represents an increase of FFA/albumin ratio of about 6-7.

FIG. 5 illustrates the morphology of the red cells in the presence of relatively advanced stages of FFA toxicity (Stage IV). The red cell population contains not only echinocytes (No. 12) but also stomatocytes (No. 14) and spherocytes (No. 15).

Stage IV (FIG. 5) cytotoxicity represents a relatively advanced form of FFA toxicity which occurs in the presence of 8-16 mEq of linoleic acid. This represents an increase of the FFA/albumin ratio of about 13-26. The cytotoxic manifestations are characterized by the fact that a proportion of the red cells develop a relatively large central depression. The surface spurs which characterized the echinocytes disappear and the cells have relatively smooth surfaces. The cells resemble red cells known as stomatocytes. In addition, some red cells assume the shape of spheres and resemble red cells known as spherocytes. Intermediate forms between stomatocytes and sphereocytes (spherostomatocytes) consisting of round cells with central slit like depressions may likewise be evident.

FIG. 6 illustrates the morphology of the red cells in the presence of very advanced stages of FFA toxicity (Stage V). All of the red cells have transformed to spherocytes (No. 15) or have lysed to form red cell ghosts (No. 16).

Stage V cytotoxicity (FIG. 6) is characterized by the almost exclusive presence of spherocytes and lysis of red cells. This occurred in the presence of 18 mEq of linoleic acid in the serum-red cell mixtures. This represents an increase of FFA/albumin ratio of about 26.

The degree of FFA toxicity in the patient will thus be determined according to the following characteristics.

A. The almost exclusive presence of discocytes and rouleux formation in the patient's blood (FIG. 1) will indicate the absence of FFA toxicity.

B. The presence of both echinocytes and discocytes in the patient's blood and the presence of echinocyte aggregates and discocytes rouleux (FIG. 2) will indicate the presence of early stage (Stage I) of FFA toxicity.

C. The almost exclusive presence of echinocytes which form aggregates in the patient's blood (FIG. 3) will indicate the presence of early to intermediate stage (Stage II) of FFA toxicity.

D. The almost exclusive presence of echinocytes which do not form aggregates in the patient's blood (FIG. 4) will indicate the presence of intermediate (Stage III) FFA toxicity.

E. The presence of stomatocytes and spherocytes (FIG. 5) in the patient's blood will indicate the presence of late stages (Stages IV-V) of FFA toxicities.

8. The results of the monitoring procedures will provide the physician or nurses in charge of the patient with important informative clues regarding the ability of the patient to handle the FFA generated by the administration of the parenteral fat emulsions. In general, the absence of FFA toxicity will suggest that the patient can handle the FFA generated by the fat emulsion. In contrast, the presence of FFA toxicity will indicate to the physician that the patient is generating toxic levels of FFA, or is unable to remove the excess FFA from the circulation. This would suggest to the physician that the rate of administration of the fat emulsion should be diminished, or that the administration of the fat emulsion should be temporarily halted. Detailed clinical decisions such as how long fat emulsion therapy should be halted or other quantitative considerations would depend not only upon the results of the present monitoring procedures, but also upon the overall status of the patient. This would vary from patient to patient and could only be determined by the physician in charge of the patient.

EXAMPLE

An example of the monitoring procedure is given in a recent publication by the author of this invention (Siegel, et al., *Journal of the American Medical Association*, volume 251, pages 1574-1579, 1984). We examined the blood of 10 patients who were receiving parenteral fat emulsions for nutritional support. Blood was examined before and after fat emulsion infusions. We found that the patient's red cells had a normal biconcave shape before infusion of the fat emulsion. Five out of 10 patients showed toxic morphologic changes of red cells after infusion of the fat emulsions. These consisted of spontaneously aggregating echinocytes in 4/10 patients and in non-aggregating spherocytes in 1/10 patients. Thus, 50% of the patients receiving parenteral fat emulsions showed no cytotoxic morphologic red cell change, 40% showed type II cytotoxic changes, and 10% showed a type IV FFA toxicity (this single patient died unexpectedly the next day of cardiac failure).

We then biochemically measured the concentrations of free fatty acids in 2 patients who showed morphologic red cell transformation and in two patients who did not show cytotoxic red cell transformations. The results showed no significant changes in the levels of free fatty acids in patients who did not exhibit red cell morphologic red cell changes. In contrast, there was an increase from 0.4 to 0.7 mEq/l of free fatty acid in the plasma of a patient with type II FFA toxicity and an increase from 0.8 to 2 mEq/l of free fatty acid in the plasma of the patient who showed type IV FFA toxicity. These observations strongly suggest that these observed morphologic red cell changes reflect free fatty acid concentrations and the free fatty acid/albumin ratio in vivo and in vitro.

While the free fatty acid monitoring method described in this study has referred to patients receiving parenteral fat emulsion, it is understood that the monitoring methods may likewise be applied to patients with other clinical conditions such as diabetic acidosis and other conditions which increase FFA levels.

What is claimed is:

1. A monitoring method for detecting free fatty acid toxicity, in a patient receiving parentaral fat emulsions, said method consisting of microscopically observing a drop of fresh blood of the patient, and comparing the morphology of the red cells in said blood, in their natural wet condition, to the morphology of red cells in serum containing known free fatty acid concentration.

2. A method as described in claim 1, wherein early stages of free fatty acid toxicity is determined by the presence of both echinocytes and discocytes in the patient's blood.

3. A method as described in claim 1, wherein early to intermediate stages of free fatty acid toxicities is determined by the almost exclusive presence of echinocytes which spontaneously aggregate in said patient's blood.

4. A method as described in claim 1, wherein intermediate stages of free fatty acid toxicity are determined by the almost exclusive presence of echinocytes which do not spontaneously aggregate.

5. A method as described in claim 1, wherein late stages of free fatty acid toxicities are determined by the presence of stomatocytes and spherocytes in said patient's blood.

6. A method of monitoring intravenous fat emulsion infusion while the fat emulsion is being infused,
said method consisting of initiating fat emulsion infusion at a rate considered to be optimal to the patient according to the clinical conditions of the patient,
obtaining a drop of blood from said patient at intervals during said infusion period,
determining the time of said intervals according to the clinical conditions of the patient,
observing said blood said a microscope and determining the morphology of red cells of said blood,
observing said red cells in their natural wet conditions,
comparing the morphology of said patient's red cells to the morphology of red cells in serum containing known free fatty acid concentrations,
and adjusting the rate of fat emulsion infusion upon the detection of free fatty acid toxicity.

* * * * *